(12) United States Patent
Schlautmann et al.

(10) Patent No.: US 7,261,824 B2
(45) Date of Patent: Aug. 28, 2007

(54) METHOD OF FABRICATION OF A MICROFLUIDIC DEVICE

(75) Inventors: Stefan Schlautmann, Enschede (NL); Albert Van den Berg, Nijverdal (NL); Johannes Gerardus Elisabeth Gardeniers, Hengelo (NL)

(73) Assignee: Micronit Microfluidics B.V., Enschede (NL)

( * ) Notice: Subject to any disclaimer, the term of this patent is extended or adjusted under 35 U.S.C. 154(b) by 602 days.

(21) Appl. No.: 10/440,515

(22) Filed: May 16, 2003

(65) Prior Publication Data
US 2003/0226604 A1 Dec. 11, 2003

(30) Foreign Application Priority Data
May 16, 2002 (EP) .................................. 02076937

(51) Int. Cl.
*C23F 1/00* (2006.01)
(52) U.S. Cl. ........................................................ 216/2
(58) Field of Classification Search .................... 216/2, 216/10, 27
See application file for complete search history.

(56) References Cited

U.S. PATENT DOCUMENTS

| | | | |
|---|---|---|---|
| 3,397,278 A | 8/1968 | Pomerantz | |
| 3,506,424 A | 4/1970 | Pomerantz | |
| 4,452,624 A | 6/1984 | Wohltjen et al. | |
| 4,944,836 A | 7/1990 | Beyer et al. | |
| 5,494,698 A * | 2/1996 | White et al. | 427/295 |
| 5,665,249 A | 9/1997 | Burke et al. | |
| 6,126,518 A | 10/2000 | Jacquinot et al. | |
| 6,258,263 B1 | 7/2001 | Henderson et al. | |
| 6,787,339 B1 * | 9/2004 | Rhine et al. | 435/173.7 |

FOREIGN PATENT DOCUMENTS

| | | |
|---|---|---|
| WO | WO 0022427 A1 | 4/2000 |
| WO | WO 0118857 A1 | 3/2001 |
| WO | WO 02024322 A3 | 3/2002 |

OTHER PUBLICATIONS

Wang H. Y. et al.: "Low Temperature bonding for microfabrication of chemical analysis devices", Sensors and Actuators B 45, 1997, pp. 199-207.

Oosterbroek, R. E. et al.: "A micromachined pressure/flow-sensor", Sensors and Actuators vol. 77, No. 3, 1999, pp. 167-177.

(Continued)

*Primary Examiner*—Parviz Hassanzadeh
*Assistant Examiner*—Roberts Culbert
(74) *Attorney, Agent, or Firm*—The Webb Law Firm

(57) ABSTRACT

The present invention relates to a method of fabricating a microfluidic device including at least two substrates provided with a fluid channel, comprising the steps of:
  a) etching at least a channel and one or more fluid ports in a first and/or a second substrate;
  b) depositing a first layer on a surface of the second substrate;
  c) partially removing the first layer in accordance with a predefined geometry;
  d) depositing a second layer on top of the first layer and the substrate surface;
  e) planarizing the second layer so as to smooth the upper surface thereof;
  f) aligning the first and second substrate;
  g) bonding the first substrate on the planarized second layer of the second substrate.

18 Claims, 6 Drawing Sheets

OTHER PUBLICATIONS

Schlautmann, S. et. al.: "Powder-blasting technology as an alternative tool for microfabrication of capillary electrophoresis chips with integrated conductivity sensors", Institute of Physics Publishing, Journal of Micromechanics and Microengineering, May 2001, pp. 386-389, vol. 11,No. 4, IOP Publishing Ltd., Printed in the UK.

Blom, M. T. et al.: "Failure Mechanisms Of Pressurized Microchannels, Model, and Experiments", Journal of Microelectromechanical Systems, Mar. 2001, vol. 10, No. 1 pp. 158-164.

Harrison, D. J. et al.: "Capillary Electrophoresis and Sample Injection Systems Integrated on a Planar Glass Chip", Anal. Chem., May 1992, 64, pp. 1926-1932, vol. 64.

A, Berthold et al. Glass-to-Glass Anodic Bonding with Standard IC Technology Thin Films as Intermediate Layers, Sensors and Actuators, vol. 82 (2000), pp. 224-228.

* cited by examiner

METHOD OF FABRICATION OF A MICROFLUIDIC DEVICE

BACKGROUND OF THE THE INVENTION

1. Field of the Invention

The present invention relates to a method of fabrication of a microfluidic device. The present invention also relates to a microfluidic device.

Recent developments in the analytical sciences have focussed on the miniaturisation of separation and detection equipment, mainly for reasons of improved performance and reduced consumption or limited availability of substances. A particular field of interest is that frequently referred to as "lab-on-a-chip", "microfluidics" or "micro total analysis systems", which is concerned with the development of instrumentation for the preparation and analysis of chemical or biological samples, the instrumentation having a format that resembles integrated micro-electronic semiconductor circuits. Originally, the developments in this field were aimed at fabrication techniques derived from the micro-electronic field to fabricate miniature separation devices. A major drawback of the systems derived from the fields are needed to establish electro osmotic or electrophoretic principles, which generally can not be sustained on a silicon substrate without electrical breakdown.

2. Brief Description of the Prior Art

Therefore today most of the used microfluidic devices for analysis or synthesis of biological and chemical species are fabricated from two flat electrically insulating glass substrates, with one substrate containing an etched microchannel and drilled or etched access-holes. The glass plates are bonded together so that the microchannel in one substrate forms together with the second glass substrate a microcapillary. In this microcapillary fluids (i.e. liquids and gasses) can be transported or stored, with the intention to perform a chemical reaction between constituents of the fluid, or to separate or mix constituents of portions of the fluid, and subsequently perform chemical or physical analysis on the constituents of the fluid, either on or of the chip. Metal electrodes are frequently integrated on or inserted into these glass chips, such electrodes serving diverse purposes such as electroosmotic or electrokinetic flow control, electrophoretic separation, or electrochemical detection. Ample illustrative examples of such devices can-be found in literature, D. J. Harrison and co-workers, in: "Capillary electrophoresis and sample injection systems integrated on a planar glass chip", Analytical Chemistry vol. 64, Sep. 1, 1992, p. 1926, describe a micromachined glass chip, which employs electrokinetic and electroosmotic principles for sample preparation and liquid propulsion, and demonstrate electrophoresis on the chip. An important issue in the fabrication of such glass devices, as well as of devices which comprise one glass substrate and one other substrate, the latter being e.g. a silicon or a polymer substrate, as well as of devices which comprise any combination of these substrate materials, is the sealing of the microfluidic capillary circuit that is formed by combining the two substrates, of which at least one contains an etched or by other means engraved channel pattern.

Some sealing methods use dispensed polymer forming liquids, such as epoxies and the such as, which are considered undesirable for fluidic chip sealing purposes for several reasons, the most important being the difficulties in dispensing a uniformly thick material layer on exact positions along the periphery of an engraved channel, the porosity and mechanical integrity of the material, and the interference of the material with e.g. organic solvents in the channel of the fluidic system during operation.

Other sealing methods are known and summarised below. The methods known for bonding of a glass substrate to a second substrate are inter alia:

1. Deposition of a thin film on one of two glass substrates followed by an anodic (also frequently called electrostatic) bonding process. This metallic or semiconducting layer can be used as intermediate layer. An example of this method is described in the article "Glass-to-glass anodic bonding with standard IC-technology thin films as intermediate layers", by A. Berthold et. al., Sensors & Actuators A Vol. 82, 2000, pp. 224-228. Described is the use of an intermediate insulator layer such as silicon nitride that acts as a sodium diffusion barrier. An advantage of these anodic bonding methods is that a roughness of several tenths of nanometers can be tolerated without a reduction in bonding quality. Drawback is the high electrical field that is required for the process, which in some cases will result in bonding of channel walls in unwanted locations.

2. Anodic bonding of a glass to a silicon substrate, for example as described in U.S. Pat. No. 3,397,278. Drawback of this method is that it can only be applied for bonding of a glass substrate to a metal or semiconducting substrate, which limits the use of the resulting devices to applications at low electrical fields and relatively low temperatures. The requirement of low temperatures, generally below about 400° C., is the result of the differences in thermal expansion that exist for most combinations of glass and metal or semiconductor substrates, and which lead to unwanted deformations of the substrate sandwich after bonding during temperature cycles.

3. Direct anodic bonding of two insulator substrates, optionally with a metal pattern in-between, as described in U.S. Pat. No. 3,506,424. This method comprises the evaporation of a thin layer of SiO on thin film circuitry, present on a substrate, and subsequent anodic bonding of a glass foil. This procedure results in a sealed electrical connection to the thin film circuitry, which circuitry partially extends to beyond the boundaries of the glass foil. Sealing is achieved because the bonding process presses the glass element on the metal line. This method generally works well for electronic applications, but may lead to unwanted leakage in fluidic applications, in particular if the chip is used at high pressures, which is relevant for separation and synthetic chemistry applications.

4. Thermal glass-to-glass bonding, which consists in heating both substrates to a temperature at which melting starts to occur, or at least to a temperature at which the glass starts to soften, e.g. at 550° C., and pressing the substrates together, by which a bond is formed. This was described in the previously mentioned publication by Harrison et al., and has as important drawbacks the occurrence of leakage when one of the substrates contains surface topography such as metal patterns and the possible deformation of the substrates when they are pressed together in a softened or partially molten state, by which the structural integrity of the fluidic circuit contained in one or both of the substrates will be affected.

5. Bonding of two glass substrates through an intermediate layer of a low-melting-point material, or through an intermediate layer which solidifies from a solution during heat treatment. Such a process is described in the article by H. Y. Wang et al., "Low temperature bonding for microfabrication of chemical analysis systems", Sensors & Act. B vol. 45, 1997, p. 199-207, in which a spin-on-glass layer is used as an adhesive that solidifies at 90° C. or after one night at room temperature. Drawback of this method is that the layer during dispension or during melting may destroy the structural integrity of the fluidic circuit, due to re-flow of the material.

Consequently, the previous methods have the disadvantages that an electric field is required for bonding, that a (partially) molten state or application of pressure is required, and/or that the method is limited to a particular choice of substrate material or film material on the substrate.

Further drawbacks of the above methods become evident from the following when sealing is required on metal patterns that are present in-between the two glass plates, between a glass plate and a silicon plate, or between two silicon plates. As discussed by Harrison et al. in the previously mentioned publication, sealing over platinum lines that extended over one of the glass substrates showed liquid leakage even after a careful heat treatment during the thermal bonding procedure. The prevention of leakage is crucial for fluidic microsystems, since leakage will give rise to cross-talk between adjacent fluidic conduits and leads to dead-volumes that give rise to cross-contamination of subsequent sample injections. Leakage is particularly important in fluidic systems which are to be used for gas analysis, systems in which gases are formed by reaction in the channel, or systems in which gas is introduced into a liquid in order to perform a chemical reaction in a chip, such as in the well-known field of microreactors for high-throughput screening of chemical substances.

It is also a requirement to have leak-tight sealing for applications that function with a high pressure inside the fluidic circuit, such as in certain well-known chromatographic methods such as High Performance (High Pressure) Liquid Chromatography (HPLC), HydroDynamic Chromatography (HDC) and some methods of Size Exclusion Chromatography (SEC).

Finally, it is also important to have leak-tight systems whenever the application of the fluidic circuit is in a harsh environment, such as under extremely high pressures or extremely low pressures. High pressures may be present underneath the earth's crust, whereas low pressures or even vacuum may be present in aerospace. Another type of harsh environment is a corrosive environment such as undersea.

One frequently pursued procedure to enhance sealing over metal patterns is that in which a recess is photolithographically defined and etched in one of the substrates, in which subsequently a metal pattern is disposed. Known is a detector integrated with the separation channel, consisting of metal lines that are partially inside and partially outside of the channel, which lines are disposed in the manner using an etched recess in one of the layers. Doing so, a modified electrostatic bonding procedure at a temperature of 350° C. allowed a seal between the layers. This known device is considered undesirable not only because of the extra photolithographic steps that are required during fabrication of the device, but even more because of the necessity of an exact dimensional match and positional alignment of the metal pattern with the etched recess. In particular, the required recess depth uniformity and metal film thickness uniformity over the substrate area, as well as the lithographic overlay quality, is difficult to obtain with most state-of-the-art etching and deposition apparatus, and can only be achieved with very well-tuned and expensive equipment. This is the reason why the method is frequently observed to fail in conventional fabrication environments, and leak-tight sealing is not obtained with the method.

SUMMARY OF THE INVENTION

It is therefore an object of the present invention to overcome at least one of the above and other drawbacks of the prior art and to provide a method of fabricating a microfluidic device with a relatively high degree of sealing in order to avoid leakage of fluid.

This object is achieved according to a first aspect of the invention in a method of fabricating a microfluidic device including at least two substrates provided with a fluid channel, comprising the steps of:
  a) etching at least a channel and one or more fluid ports in a first and/or a second substrate;
  b) depositing a first layer on a surface of the second substrate;
  c) partially removing the first layer in accordance with a predefined geometry;
  d) depositing a second layer on top of the first layer and the substrate surface;
  e) planarizing the second layer so as to smooth the upper surface thereof;
  f) aligning the first and second substrate;
  g) bonding the first substrate on the planarized second layer of the second substrate.

The first and second layer are preferably a conductive layer and an insulating layer respectively.

The method comprises a planarisation procedure, in order to keep the surface topography to an absolute minimum, so that a leak-tight bonding without loss of structural integrity can be achieved between the first substrate and any other substrate, the latter being either untreated or treated in a similar fashion as the first substrate.

The method is applied on at least one of a number of substrates that need to-be bonded together. A sequence of thin film deposition and patterning steps is performed, so that a confined conductive path (to be called a "feed-through" in the following) is obtained between the internal parts of a fluidic circuit and the outer surface of the substrate or substrates which surround the fluidic circuit. Preferably step a comprises etching of one or more contact openings in the first substrate so as to get access to said feed-throughs from outside the substrate or substrates. This provides space for electrical connectors.

In many cases the adhesion between the metal layer and the substrate is sufficient. However, in case of using a noble metal, for example Pt, Cu, Pd or Au, which has the advantage that no corrosion problems will occur, the adhesion between the metal layer and the substrate may be insufficient. Therefore step b of depositing a conductive layer comprises preferably the steps of first depositing a relatively thin adhesion layer, and then a relatively thick metal layer. The adhesion layer is made of material that will oxidize easily, for example tantalum (Ta), Chromium (Cr) or titanium (Ti). This will improve the adhesion between the substrate surface and the conductive layer. Even more preferably step b of depositing a conductive layer comprises depositing a relatively thin adhesion layer, depositing a relatively thick metal layer and depositing an additional relatively-thin adhesion layer. The additional adhesion layer is provided so as to enhance the adhesion between the metal layer and the insulating layer to be deposited in one of the following method steps. In a preferred embodiment the method comprises depositing an adhesion layer of oxidizing material, preferably Ti, Cr or Ta, with a thickness of about 5-20 nm, depositing a noble metal layer, preferably Pt, Au, Pd or Cu, with a thickness of about 100-500 nm and depositing an adhesion layer of similar oxidizing material with a thickness of about 5-20 nm.

Preferably the method comprises after step e the step of partially removing at least the insulating layer so as to expose predefined parts of the conductive layer. This provides the fluidic device with electrodes inside the channel which are, in operation, directly in contact with the fluid. These exposed electrodes enable direct contact measurements of a number of parameters. The partially removing of the insulating layer may also provide exposed parts which can be reached from outside the substrates. The earlier mentioned confined conductive path or feed-through may need to be connected to an electrical power supply. Therefore, in order to provide electrical contact between the internal parts of the conductive layer and the power supply, the insulating layer is partially removed. To the exposed parts of the conductive layer, providing access from outside the substrates, electrical connectors can be attached for electrically connecting the internal part of the fluidic circuit with the power supply.

Preferably step c of partially removing the conductive layer comprises patterning of the predefined electrode geometry in the conductive layer. This enables the microfluidic devices to be fabricated batchwise, i.e. a large number of microfluidic devices can be fabricated simultaneously. This also allows localised measurement of a number of parameters of the device, the environment of the device or the fluid contained in it.

Preferably step c of partially removing the conductive layer comprises depositing a photoresist layer on top of the conductive layer, transferring a predefined electrode pattern on the photoresist layer, and transferring the pattern by etching into the conductive layer.

Depending on the desired resolution of pattern definition and the nature of the conductive layer, preferred methods of the above step of patterning are the following.

1. a conventional photolithographic procedure, which consists of deposition of the conductive layer followed by deposition of a so-called photoresist layer, locally exposing the photoresist layer to radiation, dissolution of parts of the photoresist layer that are dissolvable after the radiation treatment (this step is commonly referred to as the development of the photoresist), and dissolution of the conductive layer from areas where the photoresist layer has dissolved; or
2. deposition of the conductive layer through a so-called shadow mask, which preferably consists of a metal foil in which openings are cut with a laser beam; or
3. a so-called lift-off process, which consists of a conventional lithographic process as described under 1, but including a step in which the surface layer of the photoresist is treated chemically to ensure an overhang after development of the photoresist, deposition of the conductive layer with a method that results in directional deposition of the layer, such that the mentioned overhang acts as a shadow mask, and finally complete dissolution of the photoresist layer, by which the conductive layer is lifted-off of the surface in areas where it is on the photoresist layer.

Preferably step d of depositing the insulating layer comprises applying a chemical vapour deposition process, wherein the insulating layer preferably is a layer of SiO2, SiN and/or SiC. In this way a dense layer of high insulating quality is achieved, which layer is suitable to be planarized in the following step of the method.

Preferably the method comprises depositing an insulating layer of a thickness equal to or, preferably, larger than the step height present on the substrate surface, i.e. larger than the total thickness of the previously deposited layer(s). In case of a thickness larger than the step height a complete encapsulation of the previously deposited layers after planarizing the insulating layer is ensured.

Preferably step e of planarizing the insulating layer comprises applying a chemical mechanical polishing (CMP) process on the insulating layer. During the planarization the insulating thickness is reduced towards the point that sufficient planarization is achieved. If a certain thickness of the insulating layer on top of the conductive layer is desired, the CMP-step may be continued until the wanted thickness is achieved.

Preferably the substrates are low temperature bonded. A preferred temperature for bonding is about 450° C. or below and typically is about 100° C. lower than the temperature needed for unpolished wafers. These relatively low temperatures reduce the chance of warping of the substrates. In some cases, for example when the substrates are nevertheless warped slightly or when the substrates have a non-uniform thickness, the bonding of the substrates is pressure assisted. Typically the pressure in this case has a value in the order of 5000 Pa.

Preferably the method comprises depositing a heating layer for heating the fluid in the channel. On this heating layer a further functional layer may be deposited, prefereably in the form of a catalytic and/or absorptive layer. This functional layer may serve purposes of enhancing a chemical reaction, absorbing a specific part of the fluid or similar processes.

According to a second aspect of the invention a microfluidic device as fabricated according to the above method is provided, wherein the first layer is arranged relative to the channel so as to influence the transport or the properties of the fluid in the channel, for example by electrical or magnetic fields or forces or by heat. Also a microfluidic device as fabricated according to the above method is provided, wherein at least a part of the first layer is arranged relative to the channel so as to form, in operational state, a detector for detecting the transport and/or the properties of the fluid in the channel. In a first preferred embodiment the second layer completely covers the detector part of the first layer so as to provide a contactless detector. In another preferred embodiment the detector part of the first layer is at least partly exposed so as to provide a contact detector, i.e. a detector which in its operational state contacts the fluid in the channel.

A further preferred embodiment relates to a device comprising a first layer that is partly exposed to the channel, the exposed parts forming electrodes for providing an electrical field in the channel. This electrical field causes transport of the fluid in the channel. This transport is called the electro osmotic flow. To ensure a sufficient pressure build up in the channel the dimensions of the channel need to be chosen relatively small, as will be explained hereafter. The width, the height, or both width and height, of fluid channel should be selected in the range of 1 nm to 2 micrometer. To provide the pressure build up dielectric material may be arranged between said electrodes in the channel. The dielectric material forms a restriction of the flow of the fluid between the inlet and outlet port and consequently causes the desired pressure build up.

In order to improve the electro osmotic flow in the channel the microfluidic device according to a further preferred embodiment not only comprises electric field electrodes (exposed to the channel), but also a gate electrode separated from the channel by the second, insulating layer. Also in the first substrate a further gate electrode, separated from the channel by a further insulating layer, may be provided. The different gate electrodes can be provided with different voltages of voltage gradients in order to influence the different liquid (shearing) flows in the channel. These shearing flows may serve the purpose of mixing the fluid enabling a chemical reaction, separation of the liquid or shear-driven chromatography.

According to another aspect of the present invention a microfluidic device is provided, comprising:

a substrate provided with a fluid channel;
a plurality of electro osmotic flow drive sections for providing electro osmotic flow in the channel, each drive section comprising electric field electrodes, exposed to the channel, and one or more gate electrodes, separated from the channel by an insulating layer, wherein the electrodes of each drive section can be controlled by control means so as to control the direction of the electro osmotic flow in the channel. As a result of putting several drive sections in series, the same electro osmotic flow rate may be obtained with the same electrical field in a longer channel than would be the case in a single electro osmotic flow drive. Or, for a fixed total channel length, for a channel build up from several sections, lower voltages are needed to obtain the electro osmotic flow rate.

The fluid channel of the microfluidic device in an embodiment of a normally-closed valve is shaped in such a way, that the fluid flow is hydraulicly restricted. Due to this particular form of the channel, leakage of liquid from the channel is avoided. An example of a particularly advantageous form of the channel is the serpentine form, as will be explained in the description of a preferred embodiment of the microfluidic device. The serpentine form enables in a further preferred embodiment a configuration wherein the negatively charged gate electrodes extend on one side of the channel and the positively charged gate electrodes extend on the opposite side of the channel. This configuration, which requires crossing of the electrodes, may be established using the above described method according to the invention.

According to another aspect of the present invention a microfluidic device is provided comprising a substrate provided with a fluid channel, electric field electrodes, exposed to the channel, and one or more gate electrodes, separated from the channel by an insulating layer, for providing an electro osmotic flow of the liquid in the channel, wherein the device also comprises one or more heater elements that are positioned on or in at least one of the walls of the channel for changing the temperature of the fluid in the channel. On top of the first or second layer, or on top of the heater elements, a functional layer may be deposited, that, in operational state, is in contact with the fluid in the channel. The functional layer comprises catalytic and/or absorptive material for the purpose of enhancing a chemical reaction and/or absorbing a part of the fluid.

The method and device according to the present invention, to be described in more detail below, makes possible a number of innovative devices that were not possible, or only possible with considerable design constraints or with serious trade-offs in the choice of materials or processing steps. One particularly important innovation is the possibility of the integration of detector elements in a micro fluidic circuit, on a high sophistication level similar to that obtained in modern micro electronic semiconductor circuitry. In this respect it is necessary to mention that one of the most widely used applications for micro fluidic devices is capillary electrophoresis, for many different applications but most famous for use in the life sciences, and that the most common detection method for this application is the Laser-Induced-Fluorescence (LIF) method, a method consisting in the emission of fluorescence from molecules present in the fluidic circuit or eluted from that circuit, which emission is stimulated by absorption of electromagnetic radiation from a laser. Both the absorbed and emitted wavelengths are characteristic of a given molecule. Because the emitted wavelength is different from the exciting wavelength, fluorescence detection is very sensitive, and in some cases approaches the detection of a single atom or molecule. Despite the fact that LIF is a sensitive, low-volume detection method for capillary electrophoresis, it has a serious drawback in the need of chemical derivatization, i.e. almost all chemical substances of interest for detection do not show fluorescence and have to be prepared to do so via a chemical reaction treatment. Furthermore, the path length dependence of LIF detection is problematic in its application to capillary electrophoresis in ultra small conduits, while also the optical detection equipment is sizeable and generally not adjustable for portable applications. Therefore other detection methods, which are equally suitable for use with capillary electrophoresis, become advantageous, such as the measurement of the conductivity at a certain location along a capillary electrophoresis separation channel. For conductivity detection a conductor has to be located as close as possible to the fluid inside the fluidic channel. Depending on how the conductivity is to be measured the electrode has to be in direct contact with the fluid (to be called "contact measurement") or it has to be insulated from the fluid by a thin insulating layer (to be called "non-contact measurement"), Such methods are well-known and described comprehensively in literature. The present invention allows easy integration and exact definition of the geometry through photolithographic techniques of such detectors, as well as of detectors of other electrochemical principles, such as amperometric or potentiometric methods, inside of a micro fluidic conduit, therewith eliminating the need for assembly of connectors between an external detector and the fluidic conduit or avoiding the insertion of bulky metal wires from the exit opening of a fluidic conduit.

Other types of detection that benefit from the present invention are optical methods, such as the well-known Surface Plasmon Resonance (SPR) method. SPR is an optoelectrical phenomenon, the basis of which is the transfer of the energy carried by photons of light to a group of electrons (a plasmon) at the surface of a very thin layer of metal, e.g. gold. The gold is coated with binding molecules, which may be antibodies, DNA probes, enzymes or other reagents chosen because they react exclusively with a specific analyte. When the coated metal is exposed to a sample that contains analyte, the analyte binds to the metal through its specific interaction with the binding molecules, leading to a change in SPR, proportional to the concentration of analyte in the sample. The present invention allows the adjustment from the outside of a fluidic chip of the electrical potential of the SPR gold layer inside of the fluidic chip.

The method also allows the integration of metallic mirrors for optical purposes, for example metal coatings to guide light in an optical absorption cell on a micro fluidic device. Still other types of detection that benefit from the present invention are magnetic methods, such as those that exploit metallic planar micro coils for the detection or generation of magnetic signals in Nuclear Magnetic Resonance in chemical analytes. Similarly, such devices can be used for generation of radio frequent signals or magnetic signals that propel magnetic beads, or manipulate living cells, or drive fluids via Magneto Hydro Dynamic propulsion.

Similarly, integrated metal patterns disposed inside of a micro fluidic conduit in the manner of the invention can be used as heaters, to stimulate a phase change such as melting of a solid or evaporation of a fluid, or to enhance a chemical reaction, in the presence or absence of a metallic or non-metallic coating that has a catalytic influence on that chemical reaction, the essential property of the method of the present invention being that the number of layers that can be stacked inside a fluidic conduit while extending partially outside of the boundaries of the fluidic conduit, is unlimited.

A particularly important class of fluidic systems that becomes feasible with the present invention is that in which electronic elements disposed inside of fluidic conduits are uses to propel or adjust fluid flow in that conduit. The well-known ElectroOsmotic Flow (EOF) principle is the result of a charge build-up at the surface of the walls that surround the conduit, which charge undergoes a drift movement when an electrical field is applied in a direction parallel to the walls, therewith exerting a drag force on the fluid, causing the fluid to move along with the charge. This principle can be used to manipulate fluid flows and in certain fluidic conduit designs can be used to generate extremely high fluid pressures. The present invention allows more advanced integration and therewith smaller dimensions of such pumps.

Fluid flow manipulation can also be achieved by influencing the mentioned charge build-up at the inner surface of the walls, which is possible with a method such as described in the article "Field-effect flow control for microfabricated fluidic networks", by R. B. M. Schasfoort et al., Science vol. 286, 1999, pp.942-945, in which a number of principles are described to use electrodes on the outside of tubular micro fluidic conduits to influence Electroosmotic flow. An essential design requirement for such a principle to work at low voltages, which for safety reasons is preferred, is that the thickness of the insulating layer which is present between the mentioned electrodes and the liquid is optimised to a value large enough to avoid electrical breakdown of the insulating layer but small enough to have a high enough field across the insulating layer to be effective to induce the desired field effect.

The present invention leads to considerable improvement of the mentioned devices, in that it allows the fabrication of micro fluidic conduits of which the inner walls are covered with one or more functional layers. In case of an electroosmotic pump as previously mentioned one metallic layer is required, which needs one or more electrical feed-throughs to the outside of the fluidic chip (cf. FIG. 2), in case of a field-effect flow controller as previously described a conductive layer covered with a high quality insulating layer is required, with at least one electrical feed-through to the outside of the fluidic chip (cf. FIG. 3).

Still other principles of propulsion or manipulation of liquids or particles suspended in liquids, that employ suspended electrodes of some kind inside of a fluidic conduit, become feasible with the present invention, such as dielectrophoresis used e.g. for transport of cells, or electrowetting which exploits the control of the contact angle between a liquid and a substrate surface by electrostatic means, or generation of gas by electrolysis which can be used to propel a liquid, or extraction of liquids from an electrospray interface at the exit opening of a fluidic chip to be used for mass spectrometry.

The application of the method is not restricted to the use of metallic or insulating materials, but can be extended to optical waveguiding materials as well. One particular example is that in which UV waveguide layers are used in conjunction with a fluidic conduit in order to perform fluorescence detection in the fluid present in the conduit. Silicon oxynitride planar waveguides can be arranged on opposite sides of a micro channel, the waveguides being exactly in line so that light from the one crosses over the channel width into the other, thereby experiencing absorption due to the presence of certain analytes in the fluid. The present invention would ensure a better bond on the surface of the waveguides and providing a tight seal of the fluidic conduit.

The method that constitutes the present invention involves inter alia: disposition of a patterned metal coating on a substrate by conventional thin film deposition methods, etching and photolithographic procedures, followed by deposition of a layer of insulating material covering the metal pattern. These processes are not new and are well-known to those working in the field of microfabrication. The next step is to planarize the substrate with a chemical mechanical polishing (CMP) process.

One of the goals of polishing in the present invention is, in addition to the planarization of the surface, to achieve a smooth surface, with a roughness so low that direct bonding between the surface and another substrate surface becomes possible. The exact value of the surface roughness that needs to be achieved depends on mechanical properties of the substrate and the layers present on it and on the surface energies of the two surfaces. Subsequently, a patterned second substrate is bonded to the first substrate, which has the smooth and planarized surface. The second substrate should also have a low surface roughness, in order to achieve the desired high bond strength. Optionally, a temperature treatment is applied, to improve the bonding strength between the two substrates even more. The CMP process according to the present invention is valid for any layer of any thickness that can be applied on a substrate with fluidic structures. The present procedure can also be extended to a larger number of layers, and a larger number of substrates.

BRIEF DESCRIPTION OF THE DRAWINGS

Further embodiments, advantages, features and details of the present invention will be elucidated in the following description of preferred embodiments thereof, with reference to the annexed figures, in which.

DETAILED DESCRIPTION OF THE PREFERRED EMBODIMENTS

Figure 1A:
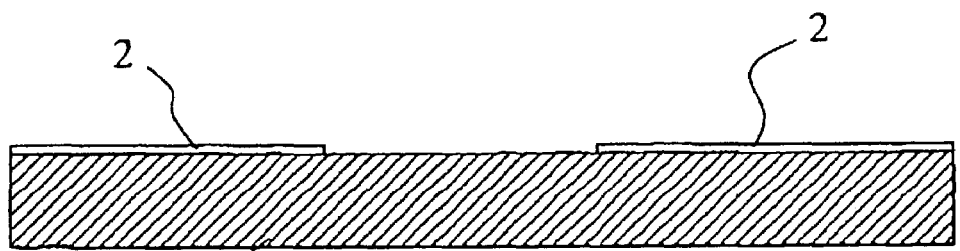
FIGS. 1a-1e show cross-sections of a preferred embodiment of a micro fluidic device fabricated according to the invention.
Figure 1B:
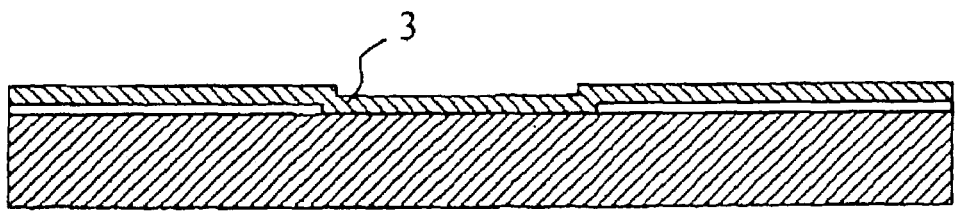
Figure 1C:
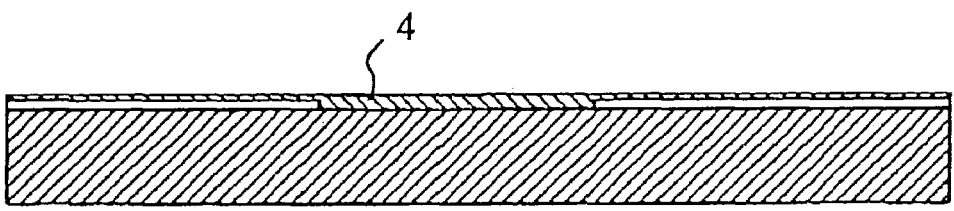
Figure 1D:
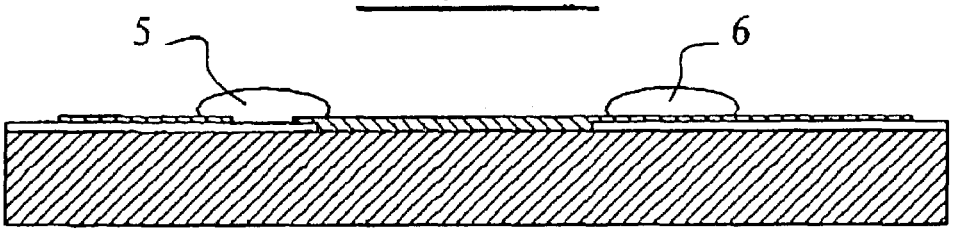
Figure 1E:
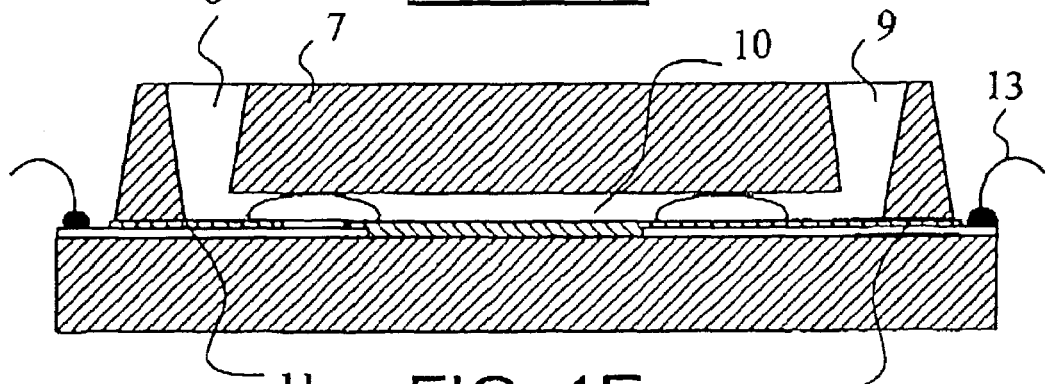

FIGS. 1A through 1E describe a preferred process sequence. FIG. 1A shows a glass substrate 1 on which a thin metal pattern 2 is applied. FIG. 1B shows the same substrate, after the deposition of a blanket layer 3 of an insulating material, preferably a PECVD silicon oxide layer. FIG. 1C shows the same substrate, after chemical mechanical polishing of the layer, so that the layer now has an atomically smooth upper surface 4. FIG. 1D shows the same substrate, after a photolithographic patterning process of the insulating layer. On this substrate, two types of sensing elements can be distinguished, a so-called "contact" detector 5, which has a defined bare area of metal in direct contact with the liquid, and which detects properties of a certain volume of liquid stretching from that detector area to a certain distance into the liquid, the volume being determined by the specific detection mechanism applied, and a so-called "contactless" detector 6, which detects properties of a certain, not necessarily the same as detector 5, volume of liquid stretching from the detector area to a certain, not necessarily the same as detector 5, distance into the liquid, the volume being determined by the specific, not necessarily the same as detector 5, detection mechanism applied. FIG. 1E shows the same substrate, bonded to a second glass substrate 7. This second substrate 7 contains a liquid inlet port 8, a liquid outlet port 9, and a liquid channel 10, in which liquid may flow over the detector areas 5 and 6. The two substrates are bonded together through the atomically (RMS<0,5 nm) smooth interface 11, which extends around the complete periphery of the second substrate 7, therewith sealing the liquid container that is composed of the liquid channel 10, the inlet and outlet ports 8 and 9, respectively, except for the openings to the inlet port 8 and the outlet port 9, present at the outer surface of substrate 7. The wire bonded electrical connectors 12 and 13 establish electrical contact with the detectors 5 and 6, respectively.

Figure 2A:
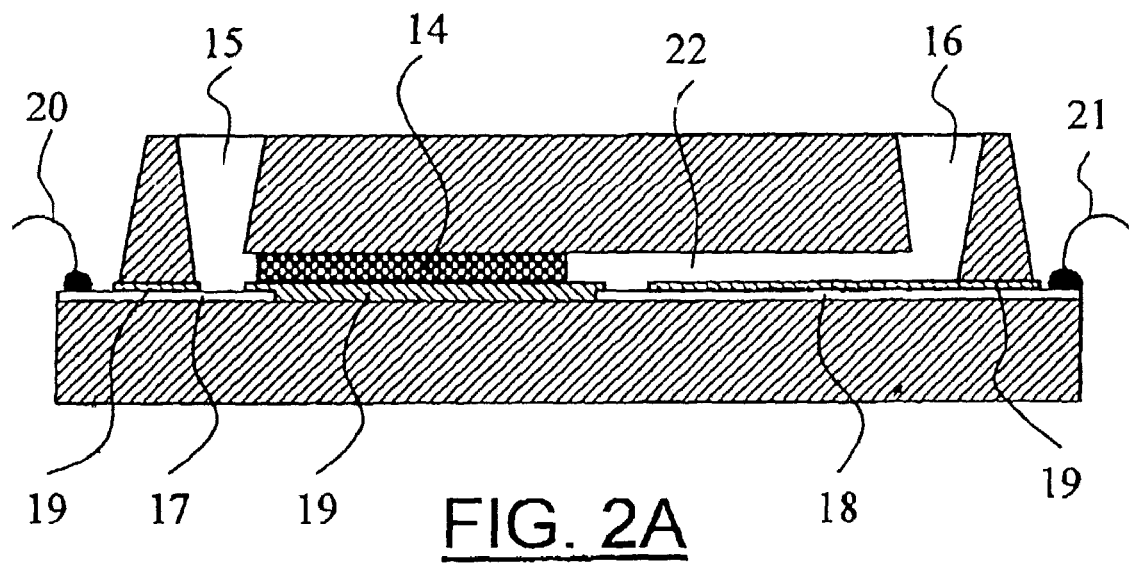
FIGS. 2a-2b show cross-sections of a second preferred embodiment of the micro fluidic device according to the invention
Figure 2B:
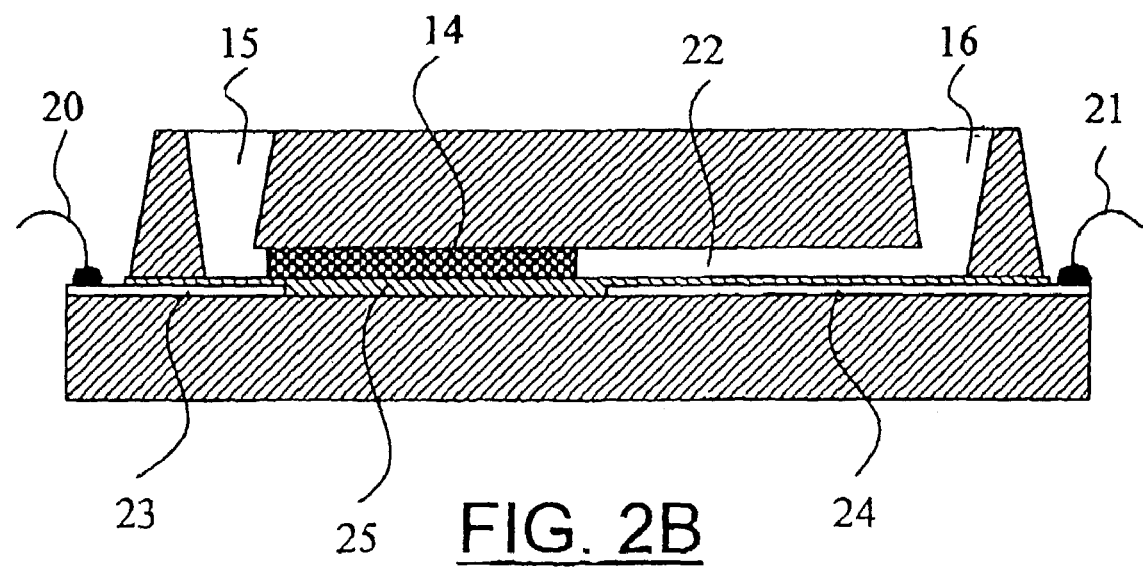

FIGS. 2A and 2B show an electroosmotic pump as known per se, however provided with an improved electrode configuration. In FIGS. 2A and 2B like elements are referred to by like reference numbers. The fabrication procedure corresponds to the procedure as described above in connection with FIG. 1, with the exception of the following. In between the inlet port 15 and outlet port 16, a porous dielectric material 14 is disposed so as to restrict the flow of the fluid between the inlet and outlet port to ensure a sufficient pressure build-up in the channel. Furthermore, in the same manner as described in FIG. 1 for detector 5, two metal electrodes 17 and 18 are disposed in the channel at specific positions in the liquid channel 22. The porous material 14 together with the electric field generated in the liquid channel 22 by the electrodes 17 and 18 serve to generate electro osmotic flow in the liquid channel 22, in the manner described in literature. Similar as described for FIG. 1, two types of electrodes are possible, a "contact type" such as denoted in FIG. 2A by 17 and 18, or a "non-contact type" such as denoted in FIG. 2B by 23 and 24. The difference between the two types is established by using a patterned insulator coating 19 in FIG. 2A, and an unpatterned coating 25 in FIG. 2B, both insulator coatings being treated by CMP to ensure a leak-tight seal between the substrates. As before in FIG. 1, wire bonded electrical connectors 20 and 21 establish electrical contact with the electrodes 17, 23 and 18, 24, respectively.

Likewise, a device of the type shown in FIGS. 2A and 2B will also function without the presence of the porous dielectric material 14, provided that either the width, the height, or both width and height, of liquid channel 22 is chosen small, i.e. in the range of 1 nm to 2 micrometer.

Figure 3A:
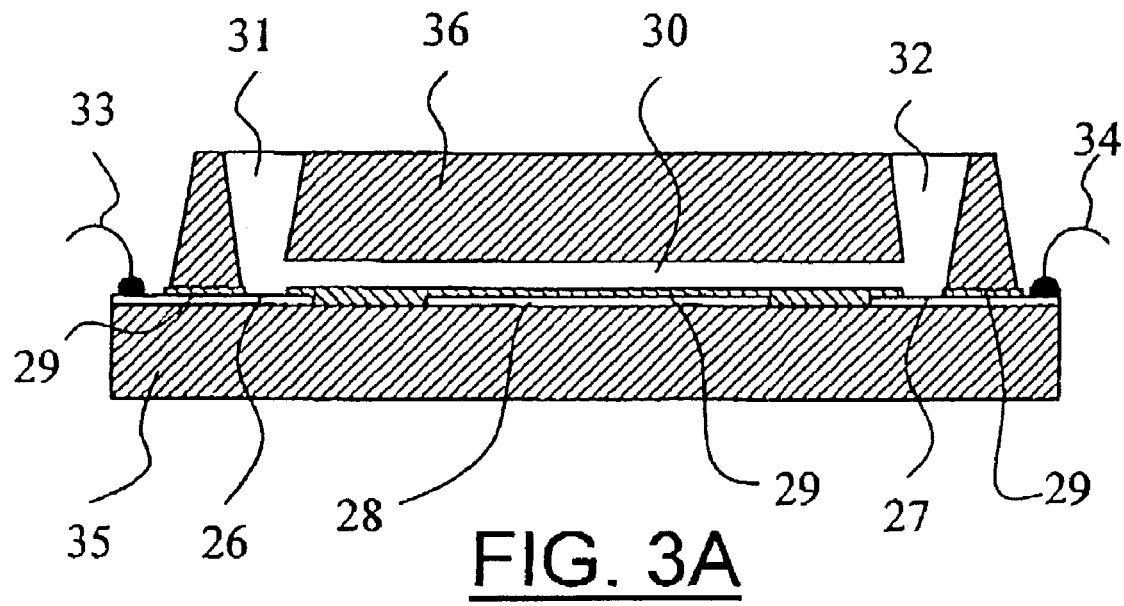
FIGS. 3a-3b show a cross-section and a top view respectively of a third embodiment.
Figure 3B:
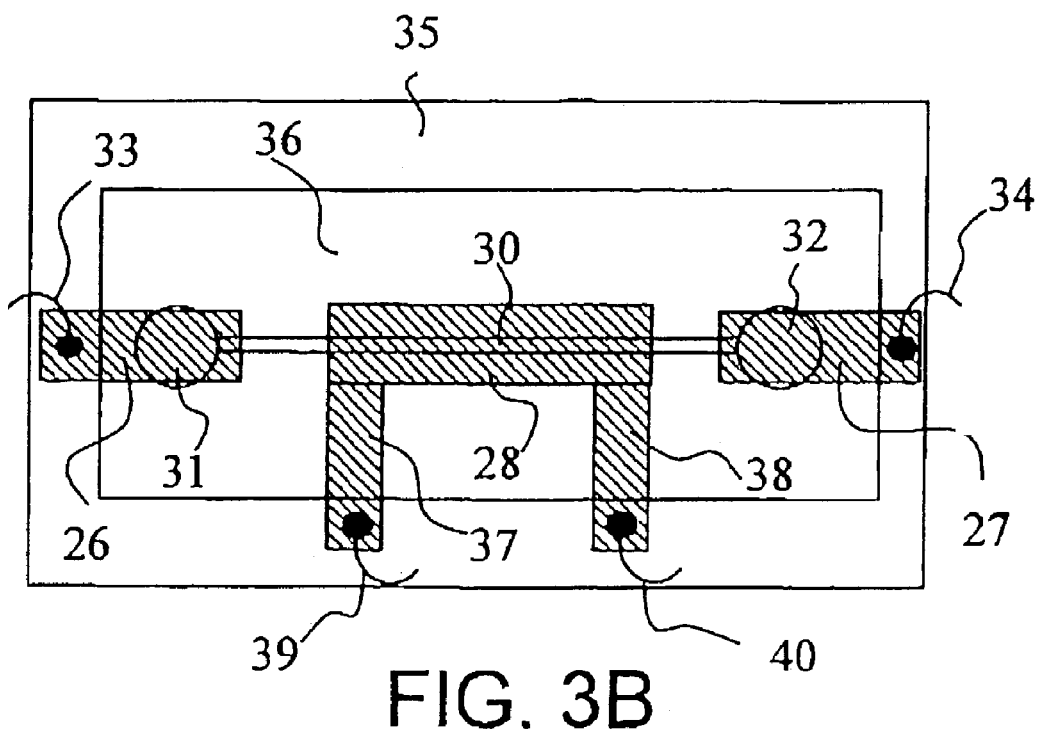

FIG. 3A and 3B describe a device that acts as the field-effect flow controller previously described and that was also referred to as a "flow-FET" in the article by Schasfoort et al., previously mentioned. The device described in FIG. 3 is of a considerably simpler design and fabrication method than in the previously mentioned publication. The device consists of two substrates 35 and 36, both of an insulating material such as glass, in which an inlet port 31 and an outlet port 32 are grafted, which connect a fluidic conduit 30. The fluidic conduit contains three electrodes of a conductive material. In the preferred embodiment two of these electrodes, 26 and 27, are of the "contact" type. The third electrode 28 is preferably larger, so as to cover most of one of the walls of the fluidic conduit 30, and is covered with a preferably thin, but high quality insulating layer 29. This layer 29 also covers other parts of the conductive material of which the electrodes 26, 27, and 28 are composed, and is treated by CMP in order to establish a leak-tight seal between the substrates 35 and 36, which is achieved according to the method described in FIG. 1. The electrode 28 serves as the "gate" of the flow-FET structure. Electrode 28 has at least one electrical feed-through (not shown in FIG. 3A) to the outside of substrate 36. However, the preferred embodiment as shown in a top view in FIG. 3B, consists of an electrode 28 with two electrical feed-throughs 37 and 38, to the outside of substrate 36, where wire bonded electrical connectors 39 and 40 establish electrical contact with the electrodes 37 and 38, respectively. The benefit of having two electrical feed-throughs to electrode 28 is that it now becomes possible to establish an electric potential gradient along electrode 28, which matches the gradient of the electric field between electrodes 26 and 27, and therewith leads to a more efficient field-effect and thus better control of the flow through the fluidic conduit 30. Electrodes 26 and 27, which are used to generate an electric field in the liquid channel 30, and thus serve to generate electro osmotic flow in that liquid channel 30, also extend to the outside of substrate 36, where wire bonded electrical connectors 33 and 34 establish electrical contact with the electrodes 26 and 27, respectively.

Figure 4A:
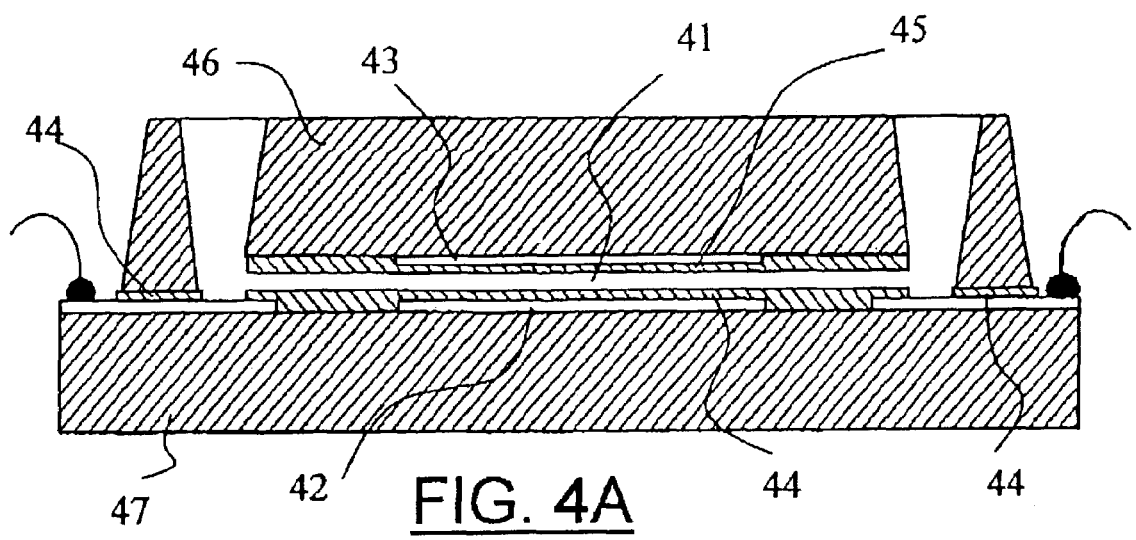
FIGS. 4a and 4b show cross-sections and FIG. 4c a top view of the fourth embodiment of the present invention.
Figure 4B:
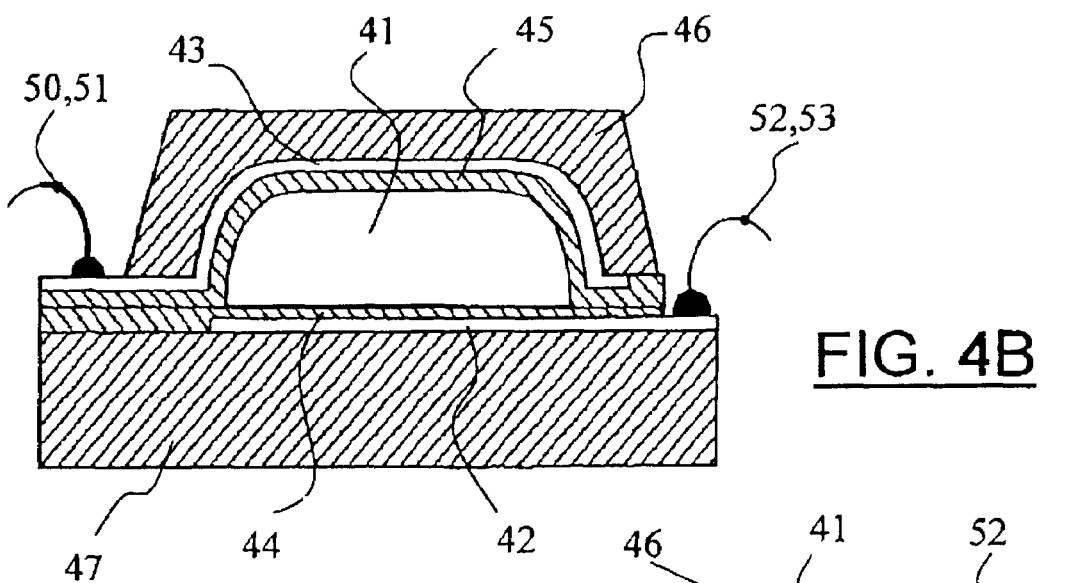

FIGS. 4A and 4B give yet another embodiment of the flow-FET device, with an even more efficient field-effect and therewith still better control of the flow through the fluidic conduit 41. As is shown in FIG. 4A, the construction of the device is basically the same as that shown in FIG. 3, except for an additional electrode 43, composed of a conductive material, which is disposed on substrate 46. The electrode 43 is covered with an insulating layer of high quality 45. This electrode 43 is disposed on the wall of the fluidic conduit 41 such that it opposes the electrode 42 which is covered with insulator layer 44. In this way, the fluidic conduit 41 can locally be completely enclosed with a field-effect generating electrode construction, which, for the case that both N electrodes 43 and 42 are adjusted to the same potential or potential gradient, leads to more efficient flow control than in the case depicted in FIG. 3. Likewise, it is also possible to adjust a potential or potential gradient to electrode 42 different from the one adjusted on electrode 43, by which it will be possible to create a gradient in the electro osmotic flow of the liquid, which flow gradient is established in the direction from electrode 42 to electrode 43 and therewith perpendicular to the direction of the electro osmotic flow in parts of the fluidic conduit outside of the area of electrodes 42 and 43. This gradient in flow will create a shearing effect that, if controlled in the proper way, can be exploited to mix liquids introduced into the fluidic conduit, or, if controlled in another way, to separate constituents of the liquid, through methods known per se.

Figure 4C:
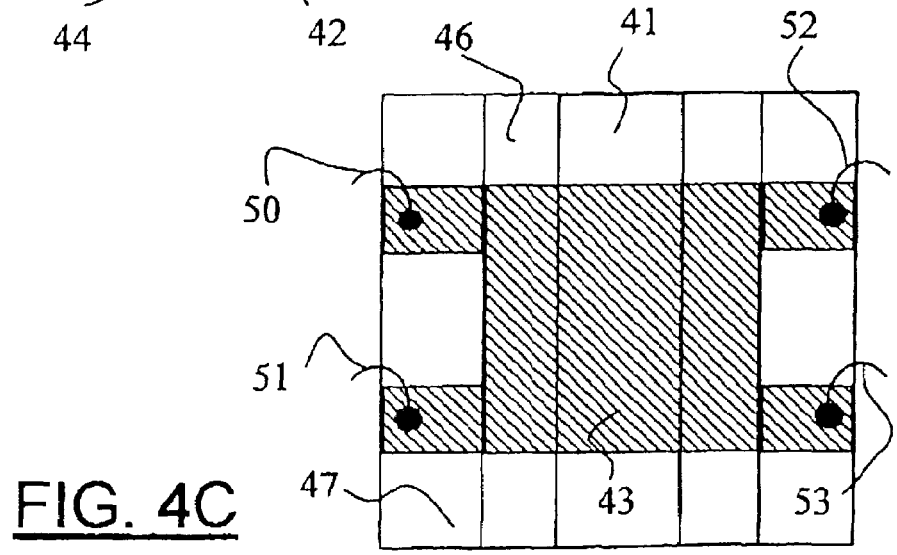

FIGS. 4B and 4C show a cross-section of the past of the fluidic conduit, where the electrodes 42 and 43 are present, and a top view of the device, respectively FIGS. 4B and 4C serve to illustrate how to wire the different electrodes to one or more voltage supplies. Connectors 50, 51, 52, and 53, are wired to supplies delivering voltages $V_A$, $V_B$, $V_C$, and $V_D$ respectively. Also, connectors 50 and 51 are connected to electrode 43, while connectors 52 and 53 are connected to electrode 42. If the voltages are chosen such that $V_A=V_C$ and $V_B=V_D$, a device of the flow-FET type as described before is obtained, with in this case a very efficient field effect. For control of the effect, either $V_A$ may be chosen equal to $V_B$, but better still is to have $V_A$ and $V_B$ (and similarly $V_C$ and $V_D$) take on such values, that a voltage gradient along the electrode 43 (and similarly along 92) arises that matches the electric field present in the fluidic conduit 41, established there due to the voltages adjusted to the electrodes at the inlet and outlet of the fluidic conduit, i.e. electrodes positioned similar to the electrodes 26 and 27 in FIG. 3. On the contrary, if the voltages are chosen such that $V_A$ and $V_C$ are different, or similarly, $V_B$ and $V_D$ are different, a shearing flow as described heretofore arises, the application of which can be very diverse, such as mixing of the liquid for the purpose of enabling a chemical reaction, or shear-driven chromatography.

Those skilled in the art of microfabrication will derive that a device as depicted in FIG. 4 will be difficult to obtain with the previously described fabrication procedure in FIG. 1, because the CMP step in that procedure will act as such that the layer constituting electrode 43 and the insulating layer 45 which is disposed on it, will be planarized in such a way that on the locations where these materials pass over the edge of the fluidic conduit machined in substrate 46, the layers will be thinned, eventually even thinned as much as to be removed completely from those locations. This effect is inherent to the CMP process. If the layers are removed partially or completely from the mentioned locations, this will affect the electrical properties of the electrode 43, and in the extreme case may even lead to a complete disconnection from the electrode 43 from one or both of the wire connectors 50 and 51. In order to prevent the mentioned unwanted planarization effect, it will be required to fill the fluidic conduit 41 with a material of properly chosen mechanical and chemical properties, subsequently perform the CMP process, and finally remove the filling material from the fluidic conduit.

Figure 5A:
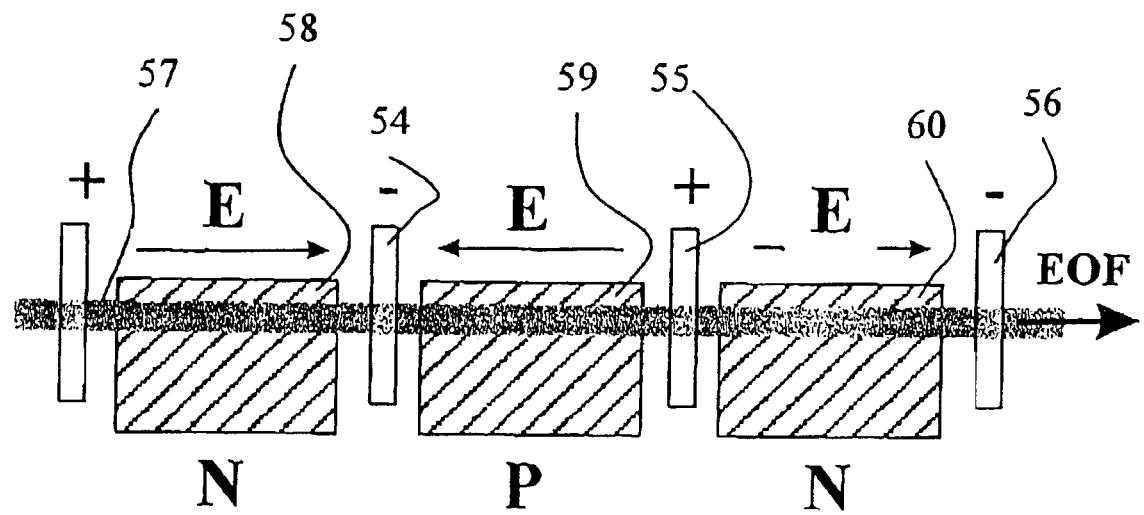
FIGS. 5a and 5b show schematically top views of further preferred embodiments of the present invention.
Figure 5B:
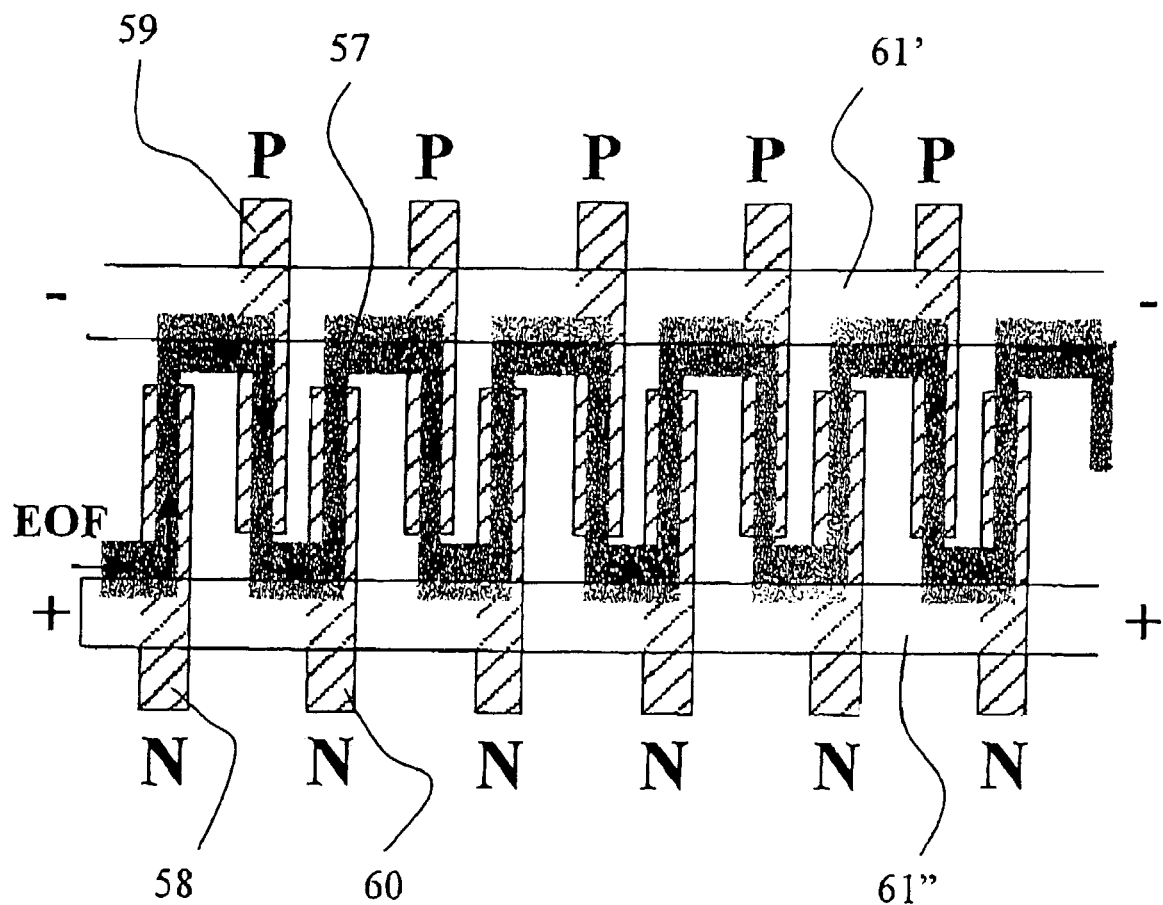

FIGS. 5A and 5B give other preferred embodiments based on the above mentioned flow-FET principle. This embodiment relates to a channel provided with a high hydraulic flow restriction. In the embodiment shown the channel is shaped such that the flow of liquid in the channel is restricted. The channel therefore remains closed and substantially no liquid can escape from the outlet opening of the channel. By providing a programmable electro osmotic flow the liquid in the channel may be forced with a preferred flow through that restriction, which will lead to a normally-closed valving device with some important advantages over conventional micro valves.

A first advantage is that the valve will have no mechanical parts, which avoids lifetime problems like wear and particle pile-up. Although particle pile-up inside or in front of the flow restriction to be developed here will alter the flow specifications of the valve, such pile-up will not change the normally-closed state of the valve, but in fact improve the leakage characteristics. This is not the case with any of the existing mechanical valves, where the leakage rate increases after particle pile-up at the valve seat.

A second advantage is that the valve according to the preferred embodiment will have a low dead volume and low power consumption.

A further advantage is that down-sizing of the device will give increased performance.

The principle of the normally-closed valving device can be explained with the following simplified theory on electroosmotic flows.

The hydraulic resistance under conditions where Poiseulle flow is present (conditions that in most microfluidic devices apply) of a fluidic channel with arbitrary cross section is given by:

$$R = \frac{2k_{shape}L\mu}{D_h^2 A} \quad (1)$$

with R the hydraulic resistance, $k_{shape}$ a shape constant (e.g. $k_{shape}$ is 16 for a capillary), L the length, $D_h$ the hydraulic diameter, and A the cross sectional area of the channel, and μ the dynamic viscosity of the liquid flowing through the channel. The electroosmotic flow through the same channel can be described by:

$$q_{EO} = \frac{\epsilon \zeta}{\mu} \frac{AV}{L} \quad (2)$$

with $q_{eO}$ the electroosmotic volume flow through the channel, ε the dielectric permittivity of the liquid, ζ the Zeta potential at the channel wall, and v the voltage along the channel length.

The optimal design of the flow restriction channel will be such, that the electroosmotic volume flow $q_{EO}$ is t highest, for an as low as possible voltage V (low voltage is one of the requirements). This will be achieved if A is high (the choice of L does not play a role, see equation 3 below). However, the hydraulic resistance should be as high as possible, to ensure a low leakage rate, which implies that the area A should be as small as possible.

A way to meet these conflicting requirements is a design consisting of N parallel channels, e.g. with a rectangular cross section of width 2a and height 2b. The choice for a rectangular shape is made on the basis of microfabrication possibilities (completely circular shapes in a flat substrate like a glass plate require more complex processing schemes), while a certain number of parallel channels may be chosen instead of a single channel, to decrease the leakage rate of the device in the closed state, or otherwise increase the flow range over which the valve can be adjusted. This point can be illustrated with a simple example.

Compare, for example, a single channel of cross-sectional area A, with four parallel and equal channels with the same total cross sectional area (i.e., each channel has an area A/4). It then follows that, if the same electric field along the channel is applied, the electroosmotic volume flow will be the same because of the same total cross sectional area. However, the hydraulic resistance of each of the four smaller channels will be sixteen times higher than that of the larger one. Just as is the case with electrical resistors, the total hydraulic resistance of four equal and parallel channels is one-fourth of the resistance of one small channel Thus, the total hydraulic resistance of the four smaller channels will be four times that of the larger channel.

Now consider an array of N parallel channels with equal cross sectional area $A_i$ and equal hydraulic resistance $R_i$. Because microfabrication techniques will be used, the number of channels can be increased easily and therefore chosen freely, but in order to fulfil requirements for a specified low leakage rate, the number should fulfil $N=R_i/R_h$ with $R_h$ the required, hydraulic resistance, as given in the specifications The electroosmotic volume flow through the total array will be:

$$q_{EO} = \frac{\varepsilon \zeta}{\mu} \frac{V}{L} NA_i = \frac{\varepsilon \zeta}{\mu} \frac{V}{L} \frac{A_i R_i}{R_h} = \frac{2\varepsilon\zeta}{R_h} V \frac{k_{shape}}{D_h^2} \qquad (3)$$

Note that the length of the channel does not play a role in the equation. We may define the last term in this equation as a "Figure Of Merit" (FOM) of the flow restriction design:

$$FOM = \frac{k_{shape}}{D_h^2} \qquad (4)$$

If this number is larger, the electro-osmotic flow will be higher. Or, if the FOM is larger, the voltage, that is required to achieve a specific volume flow rate, will be kept low. Close inspection of the details of the hydraulic properties of differently shaped channels will show that the FOM can be written as:

$$FOM = \frac{B}{a^2},$$

with B a constant depending on the shape and on the ratio between b and a (remember that the width of the individual channels is $2a$ and the height is $2b$). It thus becomes clear that $a^2$ should be Wade as small as possible, to obtain an as high as possible FOM. The exact choice of a will depend on the limitations of microfabrication.

One particular example of interest to certain biomedical applications will be given. Thus, if one takes parallel channels, each having a=2 micrometer and b=200 nanometer, which is state-of-the-art with conventional microfabrication techniques, one finds that the voltages required to achieve the desired flow rates will range from 50 to 2500 V. These voltages are too high for practical use of the proposed valve type, especially in biomedical applications like implantable devices. It is preferred to reduce these voltages to acceptable values, say a few tens of Volts, and this may be achieved by the introduction of the mentioned Flow-FET principle and the method of fabrication of the present invention.

The electroosmotic flow in a section of a channel can be reversed by applying the appropriate (i.e. of opposite sign) gate voltage $V_g$. However, if the sign of the longitudinal electrical field $\overline{E}$ along this channel section is switched as well, electroosmotic flow (EOF) will be maintained in the same direction. Thus, electroosmotic flow of a certain size and sign is possible with two different sets of conditions: i.e. positive $\overline{E}_1$, negative $V_{g,1}$; negative $\overline{E}_2$, positive $V_{g,2}$. The absolute values of $\overline{E}_1$ and $V_{g,1}$ and $\overline{E}_2$ and $V_{g,2}$, respectively, are generally not the same, but depend on the Zeta potential in the situation without any $V_g$. The Zeta potential acts as an off-set voltage for $V_g$.

Furthermore, if several of such sections are put an series, the same electro osmotic flow can be obtained with the same electrical field in a much longer channel than is possible with a conventional electro osmotic flow drive. Or, for a fixed total channel length, for a channel build up from several sections, on which the above scheme is applied, much lower voltages are needed to obtain the same value of electroosmotic flow.

One important issue with electroosmotic flow pumping yet to be solved is the potential risk of gas bubble formation by electrolysis at the electrodes, which are used to establish the electrical field $\overline{E}$ along the channel, and which may be integrated with the channels. To reduce this risk, a voltage switching scheme will be applied, in which for every channel section both the electrical field $\overline{E}$ and the wall voltage $V_g$ will be switched synchronically. This will leave the direction of the electroosmotic flow unchanged (but may give rise to periodic flow rate variations, of which the size and relevance will depend on the exact scheme and application, respectively).

The relevance of the method of fabrication of the present invention may be clarified by FIG. 5B. This figure shows the necessity of having two layers of metal wiring, which all have to be electrically insulated from one another and other parts of the embodiment by insulating film materials, and have to be separated from the fluidic conduit by the already mentioned insulating layer of which the Zeta potential will be adjusted through the flow-FET principle. The present invention allows the fabrication of such a multiple stack of thin films in a convenient and inexpensive way, with the advantages as already mentioned.

It is clear to those aquainted to the field of microfluidics and microfabrication, that the same principles as explained above may be used in other embodiments, e.g. to make normally-open valving devices or compact pumping devices an the like.

As mentioned earlier, FIGS. 5A and 5B describe a device that acts as a normally-closed valve and works according to the previously described flow-FET principle. FIG. 5A shows an embodiment to demonstrate the basic principle just described: positively (+) and negatively (−) charged electrodes ensure alternating electrical fields (E, direction indicated with arrow), which give rise to electroosmotic flow (direction indicated with arrow) in the same direction, if corresponding gates have a positive (P) or negative (N) voltage; More specifically, the device consists of several electrodes 54, 55, 56 in contact with a fluidic conduit 57. On the walls enclosing conduit 57, electrodes 58, 59, 60 are disposed, which serve as the "gates" of a number of flow-FETs connected head-to-tail. The fluidic conduit 57, the enclosing walls consisting of a thin layer of insulating material, and the electrodes 58, 59, 60 consisting of a conducting material, are preferably fabricated as described in connection with FIGS. 3A, 3B or FIGS. 4A, 4B, 4C. If the electrodes 54, 55, 56 are given electrical potentials preferably of equal value but with positive (+) of negative (−) signs according to the scheme in FIG. 5A, the "gate" electrodes 58, 59, 60 have to be adjusted to voltage values that are positive (P) or negative (N) relative to a center voltage value, to ensure a steady electro-osmotic flow through the conduit 57, as indicated with the arrow in FIG. 5A. The exact values of the voltages N and P depend on a number of parameters, such as discussed previously. Preferably the voltage values on electrodes marked "P" are the same, while also the values marked "N" are the same, but different from P.

FIG. 5B shows a preferred embodiment consisting of a long serpentine channel with several sections on which the mentioned voltage scheme is applied. The serpentine shape is chosen in order to fold the channel to a compact structure, but has the additional advantage that electronic wiring will be simplified. More specifically, the device has a fluidic conduit 57 with a serpentine shape. All electrodes marked "N" are designed such that they extend to one end of the device, while all electrodes marked "P" extend to the other end of the device. This facilitates wiring of the electrodes to external voltage or current supplies. In the embodiment of FIG. 5B the contact electrodes 54, 56 and other contact electrodes with negative voltage (not shown in FIG. 5A) of FIG. 5A are combined in one line 61' which carries a negative voltage (−), while electrode 55 and other contact electrodes with positive voltage (not shown in FIG. 5A) are combined in one line 61" which carries positive voltage (+). This preferred embodiment, which has less complex wiring and a smaller footprint than the embodiment of FIG. 5A, requires the crossing of metal electrodes, for which the method of fabrication of the present invention is the preferred method of fabrication.

For better functioning of the device it is advised that the voltages marked "+" and "−" and the "gate" voltages marked "N" and "P" are AC voltages, and switched synchronously. This will reduce the risk of gas formation by electrolysis on the electrodes that are in direct contact with the liquid.

Figure 6A:
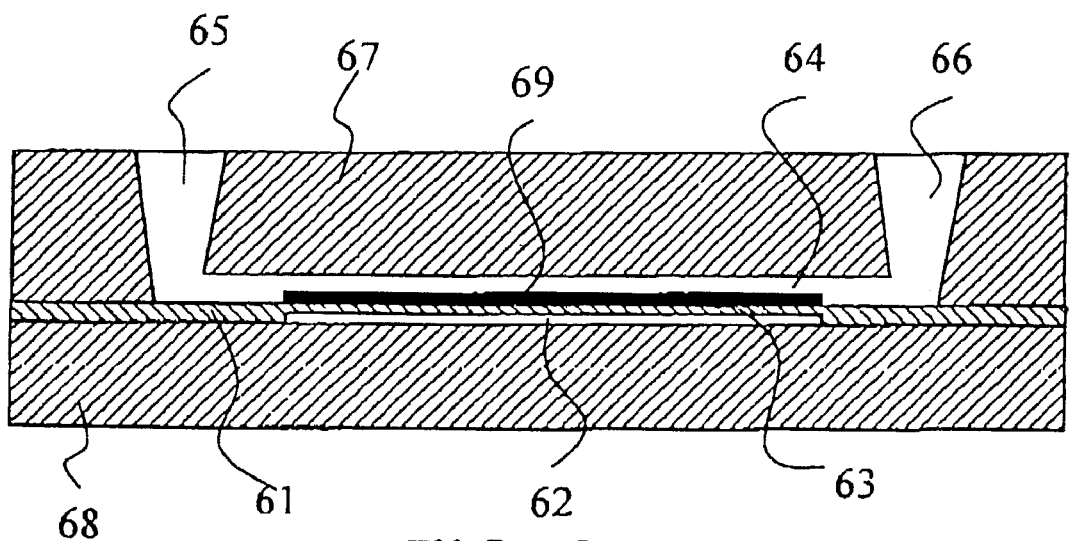
FIGS. 6a and 6b show cross-section and a top view respectively of a further preferred embodiment of the present invention.
Figure 6B:
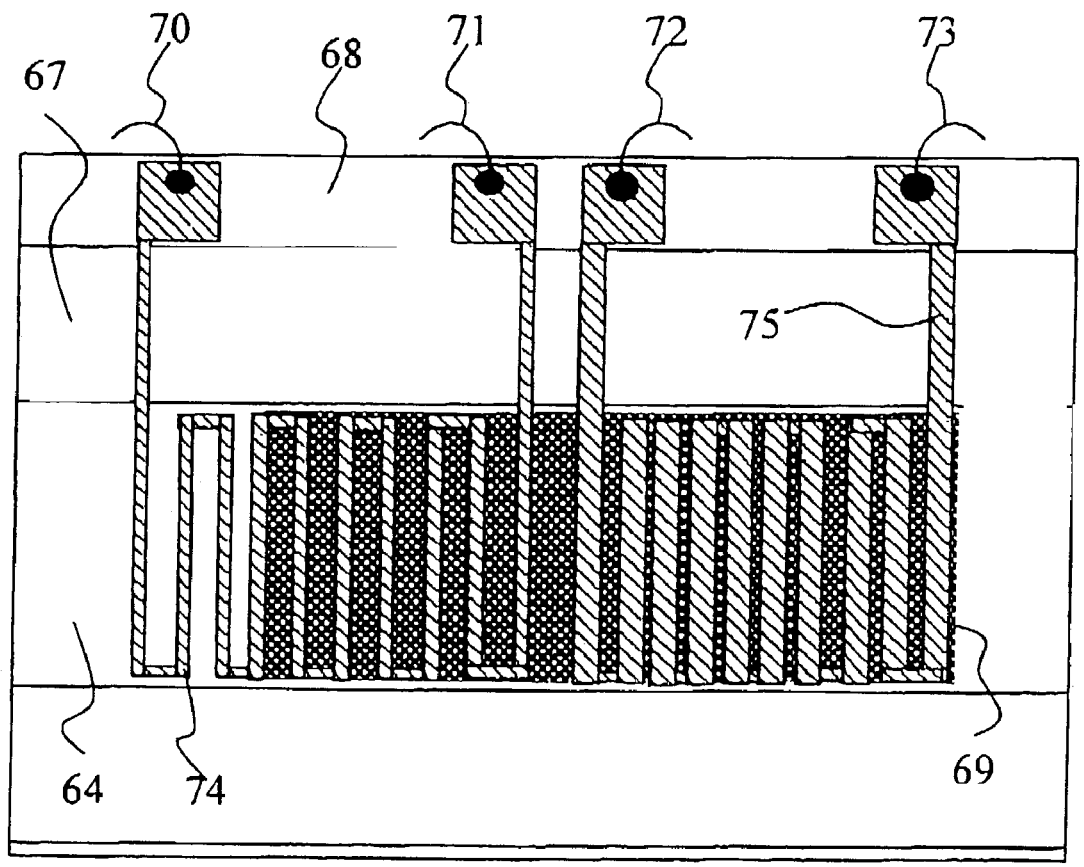

FIGS. 6A and 6B describe another embodiment that is conceivable with the method of the invention. The device comprises one or more heater elements chat are positioned on one of the walls of a fluidic conduit in order to change the temperature of the fluid that is present in or passes through the conduit. This temperature change can be used for example to activate a reaction, stimulate adsorption or desorption from or on the wall of the fluidic conduit, or influence separation or detection processes in the fluidic conduit. Optionally, a catalytic, absorptive or other type of functional layer can be deposited on the heater elements.

FIG. 6A shows a cross-section of the device, consisting of two substrates 67 and 68 that are bonded together as described previously. Substrate 67 contains a fluid inlet opening 65 and a fluid outlet opening 66, and a fluidic channel 64. The other substrate.68 contains a thin layer of a conductive material 62, that is patterned by methods previously described to result in one or more heater elements, as denoted in FIG. 6B by reference numbers 74 and 75. The conductive layer is covered with an insulating layer 63 as described previously, which is polished as described previously to enhance the bonding between the two substrates. Optionally, on the insulating layer a layer 69 is deposited and patterned, which layer may serve purposes of enhancing a chemical reaction or similar processes.

FIG. 6B gives a top view of the same device, which in this particular case contains two heater elements 74 and 75 of different geometry so as to generate a temperature gradient in the fluidic conduit, but similarly embodiments are possible with only one heater element or more than two elements.

Similarly, one of the heater elements may serve the purpose of measuring the temperature, since it is well known that certain conductors have a temperature-dependent resistivity, so by measuring the resistance of the element in ways descibed in literature, the temperature of the element may be derived. Similarly, one and the same element can be used for heating and temperature measurement.

The present invention is not limited to the above described preferred embodiments thereof; the rights sought are defined by the following claims, within the scope of which many modifications can be envisaged. In particular, it is to be noted that the term "channel" used herein encompasses any conduit, opening, duct, pipe etc. along which liquid may flow.

The invention claimed is:

1. A method of fabricating a microfluidic device including at least two substrates provided with a fluid channel, comprising the steps of:
   a) etching at least a channel and one or more fluid ports in a first and/or a second substrate;
   b) depositing a first layer on a surface of the second substrate;
   c) partially removing the first layer in accordance with a predefined geometry;
   d) depositing a second layer on top of the first layer and the substrate surface;
   e) planarizing the second layer so as to smooth the upper surface thereof;
   f) aligning the first and second substrate; and
   g) bonding the first substrate on the planarized second layer of the second substrate,
   wherein step a) comprises etching of one or more contact openings in the first substrate so as to provide space for electrical connectors.

2. The method according to claim 1, wherein step b) of depositing the first layer comprises first depositing a relatively thin adhesion layer, and then a relatively thick metal layer.

3. The method according to claim 1, wherein step c) of partially removing the first layer comprises patterning of a predefined electrode geometry in the first layer.

4. The method according to claim 1, comprising depositing an insulating layer of a thickness equal to or, larger than a step height present on the substrate.

5. The method according to claim 1, wherein the substrates are pressure assisted and/or low temperature bonded.

6. The method according to claim 1, comprising fabricating a plurality of microfluidic devices on said substrates and separating the substrates into the individual microfluidic devices.

7. The method according to claim 1, comprising the step of depositing a heating layer for heating a fluid in the channel.

8. The method according to claim 7, comprising the step of depositing a functional layer, formed as a catalytic and/or absorptive layer on the heating layer.

9. The method according to claim 1, wherein the first layer is a conductive layer and the second layer is an insulating layer.

10. The method according to claim 9, wherein step a) of etching a channel involves chemical wet etching, dry etching and/or power blasting techniques.

11. A method of fabricating a microfluidic device including at least two substrates provided with a fluid channel, comprising the steps of:
   a) etching at least a channel and one or more fluid ports in a first and/or a second substrate;
   b) depositing a first layer on a surface of the second substrate;
   c) partially removing the first layer in accordance with a predefined geometry;

d) depositing a second layer on top of the first layer and the substrate surface;
e) planarizing the second layer so as to smooth the upper surface thereof;
f) aligning the first and second substrate; and
g) bonding the first substrate on the planarized second layer of the second substrate,
wherein step b) of depositing a conductive layer comprises depositing a metal layer and wherein step b) of depositing the first layer further comprises depositing a relatively thin adhesion layer, depositing a relatively thick metal layer and depositing an additional relatively thin adhesion layer.

12. The method according to claim 11, comprising depositing an adhesion layer of oxidizing material, comprising Ti, Ta, Cr or any combination thereof, with a thickness of about 5-20 nm, depositing a metal layer with a thickness of about 100-500 nm, and depositing an adhesion layer of similar oxidizing material with a thickness of about 5-20 nm.

13. A method of fabricating a microfluidic device including at least two substrates provided with a fluid channel, comprising the steps of:
a) etching at least a channel and one or more fluid ports in a first and/or a second substrate;
b) depositing a first layer on a surface of the second substrate;
c) partially removing the first layer in accordance with a predefined geometry:
d) depositing a second layer on top of the first layer and the substrate surface;
e) planarizing the second layer so as to smooth the upper surface thereof;
f) aligning the first and second substrate; and
g) bonding the first substrate on the planarized second layer of the second substrate, after step e) comprising the step of partially removing at least the second layer so as to expose predefined parts of the first layer.

14. The method according to claim 13, wherein the exposed parts of the first layer are, in an operational state, in direct contact with a fluid in the channel so as to provide a contact detector.

15. The method according to claim 13, wherein the exposed parts of the first layer are arranged so as to be accessible from outside the substrate(s).

16. A method of fabricating a microfluidic device including at least two substrates provided with a fluid channel, comprising the steps of:
a) etching at least a channel and one or more fluid ports in a first and/or a second substrate;
b) depositing a first layer on a surface of the second substrate;
c) partially removing the first layer in accordance with a predefined geometry;
d) depositing a second layer on top of the first layer and the substrate surface;
e) planarizing the second layer so as to smooth the upper surface thereof;
f) aligning the first and second substrate; and
g) bonding the first substrate on the planarized second layer of the second substrate,
wherein step d) of depositing the insulating layer comprises applying a chemical vapour deposition process, the second layer comprising a layer of $SiO_2$, SiN and/or SiC.

17. A method of fabricating a microfluidic device including at least two substrates provided with a fluid channel, comprising the steps of:
a) etching at least a channel and one or more fluid ports in a first and/or a second substrate;
b) depositing a first layer on a surface of the second substrate;
c) partially removing the first layer in accordance with a predefined geometry:
d) depositing a second layer on top of the first layer and the substrate surface;
e) planarizing the second layer so as to smooth the upper surface thereof;
f) aligning the first and second substrate; and
g) bonding the first substrate on the planarized second layer of the second substrate,
wherein step e) of planarizing the insulating layer comprises applying a chemical mechanical polishing process on the second layer.

18. A method of fabricating a microfluidic device including at least two substrates provided with a fluid channel, comprising the steps of:
a) etching at least a channel and one or more fluid ports in a first and/or a second substrate;
b) depositing a first layer on a surface of the second substrate;
c) partially removing the first layer in accordance with a predefined geometry;
d) depositing a second layer on top of the first layer and the substrate surface;
e) planarizing the second layer so as to smooth the upper surface thereof:
f) aligning the first and second substrate; and
g) bonding the first substrate on the planarized second layer of the second substrate, the method further comprising the steps of filling the channel and/or the ports with filler material, planarizing the second layer and removing the filler material.

* * * * *